United States Patent
Jacobs et al.

(10) Patent No.: US 6,211,409 B1
(45) Date of Patent: Apr. 3, 2001

(54) PROCESS FOR PREPARING MONO-, DI- OR OLIGOAMIDE ALKOXYLATES

(75) Inventors: Ulrike Jacobs, Haltern; Uwe Kaltwasser, Marl; Klaus Kwetkat, Lünen; Ernst-Jürgen Lehmann, Dülmen, all of (DE)

(73) Assignee: RWE-DEA Aktiengesellschaft fuer Mineraloel und Chemie, Hamburg (DE)

( * ) Notice: Subject to any disclaimer, the term of this patent is extended or adjusted under 35 U.S.C. 154(b) by 0 days.

(21) Appl. No.: 09/214,052

(22) PCT Filed: Aug. 28, 1996

(86) PCT No.: PCT/EP96/03776

§ 371 Date: Aug. 27, 1999

§ 102(e) Date: Aug. 27, 1999

(87) PCT Pub. No.: WO98/00392

PCT Pub. Date: Jan. 8, 1998

(30) Foreign Application Priority Data

Jun. 28, 1996 (DE) ............................................. 196 25 937

(51) Int. Cl.$^7$ ................................................... C07C 231/00
(52) U.S. Cl. ............................................ 564/134; 564/138
(58) Field of Search ....................................... 564/138, 134

(56) References Cited

FOREIGN PATENT DOCUMENTS

| 4440328 | 5/1996 | (DE) . |
|---|---|---|
| 0038862 | 11/1981 | (EP) . |
| 835566 | 5/1960 | (GB) . |
| 2203177 | 10/1988 | (GB) . |
| WO 95/19955 | 7/1995 | (WO) . |

*Primary Examiner*—Porfirio Nazario-Gonzalez
(74) *Attorney, Agent, or Firm*—Browning Bushman

(57) ABSTRACT

A process is disclosed for preparing di- or oligoamide alkoxylates. Diamides are prepared from carboxylic acids or carboxylic acid alkyl esters and di-, oligo-, or polyamines and are alkoxylated as a melt directly after their preparation, without any further intermediate preparation process.

14 Claims, No Drawings

PROCESS FOR PREPARING MONO-, DI- OR OLIGOAMIDE ALKOXYLATES

For the preparation of carboxylic acid diamide alkoxylates or -oligoamide alkoxylates described in WO 95/19955, or of carboxylic acid diamide- or -oligoamide polyalkylene ether sulfates as described in DE 44 40 328 it is essential to have available a raw material having the highest possible purity, very few coloring impurities, and the required basic structure in order to obtain the desired properties and effectiveness of the surfactants or formulations prepared therefrom.

EP-A-0 038 862 describes the preparation of an effective fabric softener by reacting diethylene triamine or a higher homologue thereof with two molar proportions of fatty acid, followed by monoethoxylation of the amine nitrogen in the resultant product and at least partial neutralization with a lower organic acid and/or sulfur dioxide.

The preparation of the structure described in detail in WO 95/19955 is disclosed in an example given therein which is reported to be also representative of other structures claimed therein. Said example teaches a three-step process wherein the amine is first reacted with one mole of ethylene oxide per primary or secondary amino group in the molecule, followed by acylation of the secondary α- and ω-amino groups with carboxylic acid methyl ester and, in the third step, by reaction with the remaining alkoxy units required for the end product.

However, the expert knows that said process yields a mixture of any theoretically obtainable products wherein the gemini polyether fatty acid amides corresponding to the claimed structure can only be present in concentrations of $\leq 50$ mole-% in this product mixture and, in contrast thereto, larger quantities of amine alkoxylate fatty acid esters are inevitably present in the product. It is true that said process facilitates the handling of di- and oligoamides which frequently have high melting points, but on the other hand, the product quality is significantly affected.

The process described in DE 44 40 328 employs di- or oligoamides prepared by reacting amines with free carboxylic acids or carboxylic acid methyl esters. However, particularly when using alkylene diamines, but also when employing other spacer units of which, furthermore, oxygen-containing compounds have limited temperature stabilities, the problem arising therefrom is that the diamides prepared by said process must be remelted after their preparation which has an adverse effect on quality and color of the products.

The use of mono- or diethanol amines for amidation, a method employed for preparing conventional fatty acid polyether—and fatty acid polyether sulfate amides, is not practicable in the cases described hereinabove, because the amines are employed for linking two carboxylic acid chains.

We have surprisingly found that the problems and quality deteriorations described hereinabove are avoided, when alkoxylating the diamides as a melt immediately after their preparation and without any intermediate treatment or isolation. The catalyst employed for the amidation can be further used for the alkoxylation, or, prior to alkoxylation, i.e. a reaction with ethylene- and/or propylene oxide, optionally followed by a reaction with butylene oxide, an additional quantity of catalyst can be added or a different catalyst can be employed. The object of this invention is a process for preparing di- or oligoamide alkoxylates, characterized in that diamides are prepared from carboxylic acids or carboxylic acid alkyl esters and di-, oligo-, or polyamines and are alkoxylated as a melt immediately after their preparation without any intermediate isolation or treatment. When using free carboxylic acids, no catalyst is required in which case the alkoxylation catalyst is added after the amidation is terminated.

The reactions can be performed in one pot or, alternatively, in two different reactors. Expediently, the two reactors should be place(i close to each other, but when employing heated lines, even a greater distance in principle will not constitute a problem for the process of the invention.

Said process is characterized in that carboxylic acids or carboxylic acid methyl esters having 4 to 24, preferably 8 to 18 carbon atoms in the initial carboxylic acid and mixtures thereof are placed into the pot and the di-, oligo-, or polyamine is admixed thereafter. The carbon chain of the carboxylic acids or carboxylic acid methyl esters can be branched or unbranched, cyclic or acyclic, aliphatic or aromatic. Any of the amines described in DE 44 40 328 and WO 95/19955 may be employed as di-, oligo-, or polyamine in the process of the invention. The only prerequisite for the mixture is that the components be placed in a liquid state into a suitable reactor. Each step is made under a nitrogen blanket. In order to ensure high color quality, it is essential to largely exclude atmospheric oxygen. The catalyst, if necessary, is added last, because otherwise, e.g. in case carboxylic acid methyl esters are used, the starting material would be saponified. Suitable catalysts are those used for amidation, e.g. potassium methanolate, sodium methanolate, potassium hydroxide, sodium hydroxide, tin oxalate, elementary tin, zinc oxide, and potassium tert-butanolate. Sodium—and potassium alcoholates and -hydroxides are particularly preferred. The catalyst is used in quantities of 0 to 5, preferably 0 to 3, most preferably 0 to 1 percent by weight, referring to the total batch (subjected to amidation).

Once the reactants are mixed, the internal reactor temperature is increased to at least 2 to 5° C. above the solidification temperature of the diamide product and to max. 240° C., preferably 80 to 200° C., most preferably 100 to 190° C. Alternatively, removal of water or methanol, depending on the starting material, is immediately started, or is begun once the head and bottom temperatures are constant, i.e. when the reaction equilibrium is established. The required temperatures depend on the actual starting materials mixture. They are in the aforementioned range. The time requirement is from 10 to 120 minutes, preferably 15 to 60, most preferably 15 to 40.

Methanol or water are removed at atmospheric pressure, while introducing a slow stream of nitrogen into the reaction mixture, or they are removed under vacuum. In order to increase the selectivity, it is expedient to build in several devices resulting in a separation efficiency of 0.1 to 20, preferably 0.5 to 10 theoretical separating trays.

After the methanol or water has been removed, the temperature is adjusted to 2 to 5° C. above the solidification point of the amide product, but not below 90° C., preferably to 130 to 180° C. Catalyst can now be added. Suitable catalysts are those employed for alkoxylations, including catalysts resulting in narrow distributions of homologues, e.g. sodium—and potassium alkoxylates and—hydroxides, phyllosilicates, and hydrotalcite. Sodium—and potassium alkoxylates and—hydroxides are preferred.

The alkoxylation is carried out as known in the art using the required amount of alkylene oxide at a total pressure of 2 to 6 bar and temperatures of 100 to 190° C., preferably 130 to 185° C. When the after-reaction is complete, the product is discharged at temperatures of 40–160° C., preferably 45 to 120° C. If it is intended to use the alkoxylate as a surfactant, the catalyst, e.g. low-molecular carboxylic acids, such as lactic acid, must be neutralized. When employing heterogeneous catalysts, subsequent filtration is necessary. If the alkoxylate is employed as such, it can be bleached, if necessary, for instance with hydrogen peroxide.

In case of subsequent sulfation, e.g. as described in DE 44 40 328, no neutralization is necessary. For said sulfation an $SO_3$/air mixture or oleum or chlorosulfonic acid or amidosulfonic acid, preferably an $SO_3$/air mixture can be employed. Thereafter, the product is neutralized with the corresponding equivalents of alkali—or alkaline earth hydroxides or the corresponding equivalents of mono-, di-, and trialkanol amines. As a result of the gentle preparation of the precursors, products having high color qualities and the desired structures can be obtained even after this process step. Optionally, said step may be followed by bleaching, e.g. with hydrogen peroxide.

The process of the invention is outstanding in that it allows to prepare the structures described in DE 44 40 328 and WO 95/19955 in high purities of greater than 70 mol-", preferably more than 80 mol-%, most preferably more than 85 mol-% and, consequently, to obtain more effective surfactants or formulations which are furthermore less expensive. The structures described in DE 44 40 328 have the general formula:

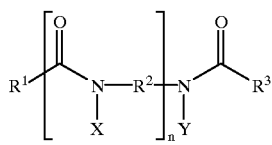

(I)

wherein $R^1$ and $R^2$, independently of one another, are a hydrocarbon radical with 1 to 22 carbon atoms, $R^2$ is a bridging group, X and Y, independently of one another, are substituents, and n is the degree of oligomerisation of from 1 to about 10.

The process of the invention will be described in greater detail by the following examples which, however, shall not be regarded as a limitation thereof.

EXAMPLE 1

| | |
|---|---|
| 203.9 kgs of $C_8/C_{10}$ fatty acid methyl ester | 1.20 kmol |
| 36.1 kgs of ethylene diamine | 0.60 kmol |
| 2.4 kgs of K-methylate powder | |
| 264 kgs of ethylene oxide | 6.00 kmol |

The fatty acid methyl ester and the amine were combined in an appropriate 1,000-liter reactor. Then the catalyst was added. The mixture was heated to reflux which started at a bottom temperature of approx. 115° C. The reaction equilibrium was established after about 45 minutes, and the bottom and head temperatures set in at about 102° C. and 65° C., respectively. The resultant methanol was distilled off, while the bottom temperature increased to 175° C.

After switching the apparatus to the ethoxylation mode, the reaction continued immediately. At a reaction temperature of 165° C., nitrogen was pressed in at 0.5 bar and supplemented with ethylene oxide such that the pressure increased to 3.0 bar at which level it was maintained by continuous addition of ethylene oxide. After about 1.5 hours, take-up of the prescribed ethylene oxide quantity was complete. The after-reaction took one hour during which time the reactor pressure dropped to approx. 1 to 1.5 bar. Thereafter, residual ethylene oxide was blown out using nitrogen, followed by draining the reaction product while purging with nitrogen. The resultant light-colored product had an iodine color number of 27 and, as shown by $^{13}C$ NMR analysis, had the required structure.

EXAMPLE 2

| | |
|---|---|
| 203.9 kgs of $C_8/C_{10}$ fatty acid methyl ester | 1.20 kmol |
| 44.5 kgs of 1,2-diaminopropane | 0.60 kmol |
| 2.4 kgs of K-methylate powder | |
| 264 kgs of ethylene oxide | 6.00 kmol |

The fatty acid methyl ester and the amine were combined in an appropriate 1,000-liter reactor. Then the catalyst was added. The mixture was heated to reflux which started at a bottom temperature of approx. 120° C. The reaction equilibrium was established after about 40 minutes, and the bottom and head temperatures set in at about 106° C. and 70° C., respectively. The resultant methanol was distilled off, while the bottom temperature increased to 180° C.

After switching the apparatus to the ethoxylation mode, the reaction continued immediately. At a reaction temperature of 165° C., nitrogen was pressed in at 0.5 bar and supplemented with ethylene oxide such that the pressure increased to 3.0 bar at which level it was maintained by continuous addition of ethylene oxide. After about 1.5 hours, take-up of the prescribed ethylene oxide quantity was complete. The after-reaction took one hour during which time the reactor pressure dropped to approx. 1 to 1.5 bar. Thereafter, residual ethylene oxide was blown out using nitrogen, followed by draining the reaction product while purging with nitrogen. The resultant light-colored product had an iodine color number of 28 and, as shown by $^{13}C$ NMR analysis, had the required structure.

What is claimed is:

1. A process for preparing di- or oligo amide alkoxylates characterised in that carboxylic acids or carboxylic acid alkyl esters are reacted with di-, oligo- or polyamines and are alkoxylated as a melt immediate after reaction without any intermediate isolation or treatment to produce compounds according to formula (I):

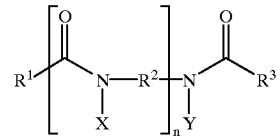

(I)

wherein $R^1$ and $R^2$, independently of one another, are a hydrocarbon radical with 1 to 22 carbon atoms, $R^2$ is a bridging group, X and Y, independently of one another, are substituents, and n is the degree of oligomerisation of from 1 to about 10.

2. A process according to claim 1,
characterized in that
carboxylic acids or carboxylic acid alkyl esters having 4 to 24, preferably 8 to 18, carbon atoms in the hydrocarbon residue of the initial carboxylic acid are used.

3. A process according to claim 1, characterized in that di-, oligo-, or polyamines are employed.

4. A process according to claim 1, characterized in that the catalyst used for the amidation is also employed for the alkoxylation.

5. A process according to claim 1, characterized in that no catalyst is added for the amidation in case carboxylic acids are used.

6. A process according to claim 1, characterized in that a catalyst that is different from the one used for the amidation is employed or added for the alkoxylation.

7. A process according to claim 1, characterized in that the components are charged to the reactor in a liquid condition.

8. A process according to claim 1, characterized in that amidation and alkoxylation are performed as a one-pot process.

9. A process according to claim 1, characterized in that the internal reactor temperature is increased to at least 2° C. above the solidification temperature of the amide product and to max. 240° C., preferably 80 to 200° C.

10. A process according to claim 1, characterized in that the products are subjected to bleaching.

11. A process according to claim 1, characterized in that the compounds are obtained in purities of greater than 70 mol-%.

12. A process according to claim 1 characterized in that the compounds are obtained in purities of greater than 85 mol-%.

13. A process according to claim 1, characterized in that exclusively the nitrogen atoms of the amide groups of the di- or oligoamide alkoxylates are alkoxylated in the presence of an alkoxylation catalyst.

14. A process according to claim 1, characterized in that alkylendiamines having 2 or 3 carbon atoms and two primary amine groups, in particular 1,2-ethylendiamine or 1,2-diaminopropane, are employed in the reaction.

* * * * *